US005836998A

United States Patent [19]

Mueller et al.

[11] Patent Number: 5,836,998

[45] Date of Patent: Nov. 17, 1998

[54] ADHESIVE STENCIL FOR BODY ART

[76] Inventors: Linda Mueller, 2720 H N. Greenview, Chicago, Ill. 60614; Beata R. deVirion, 1037 Des Plaines Ave., #303, Forest Park, Ill. 60130

[21] Appl. No.: 947,004

[22] Filed: Oct. 8, 1997

[51] Int. Cl.$^{6}$ .................................................... A61N 33/00

[52] U.S. Cl. ............................. 607/95; 101/35; 101/126; 101/129; 132/319; 132/333

[58] Field of Search .............................. 607/95; 132/319, 132/333; 600/556; 101/129, 35, 126

[56] References Cited

U.S. PATENT DOCUMENTS 5,052,418 10/1991 Miller ..................................... 132/319

5,470,351 11/1995 Ross et al. ................................ 607/95

*Primary Examiner*—Terressa Mosley

*Attorney, Agent, or Firm*—Welsh & Katz, Ltd.

[57] ABSTRACT

A method and apparatus for allowing a decorative stain to be applied to a predetermined epidermal area of a subject is disclosed. An adhesive stencil having an adhesive layer and a generally non-absorbent layer substantially coextensive therewith about a decorative pattern is temporarily secured to a predetermined epidermal area to allow a decorative stain to be applied thereon by the steps of applying a predetermined amount of a material that is capable of staining the epidermis to said generally non-absorbent layer, allowing said epidermal stain material to dry and removing said stencil and said epidermal stain material from said predetermined epidermal area.

4 Claims, 1 Drawing Sheet

ADHESIVE STENCIL FOR BODY ART

FIELD OF THE INVENTION

The present invention generally relates to the application of a staining material such as a henna-based dye to the epidermis for cosmetic purposes and, more particularly, to a system that allows the dye or stain to be applied by an inexperienced operator through an adhesive stencil.

BACKGROUND OF THE INVENTION

Henna based dyes or stains are utilized to apply various designs to temporarily decorate the epidermis. This is done by applying the paste directly to the epidermis, either free hand or through the use of a stencil. These methods can be difficult to use for the novice. The free hand method takes experience, control, is time consuming and expensive. Stencils can leak and are hard to keep in place.

Mehndi is an art form in which henna based epidermal dye is applied to stain the skin in decorative patterns and has been known for many centuries. This art form is still used primarily in Middle Eastern and Asian cultures before a celebration such as a wedding for a festival. For example, Hindu women have intricate designs applied to their palms and sole of their feet prior to their wedding because, for example, it is believed that the designs enhance fertility and the chance that the young couple will have children. Others say that the decorative patterns are aesthetically pleasing and enhances the beauty of the bride.

After the henna past is applied to the skin and allowed to dry, it will stain the epidermal layer of the skin in direct contrast to a tattoos in which the entire dermis is stained. The epidermis, or outer layer of the skin, naturally sloughs off and takes the Mehndi design with it. In effect, the individual has a tattoo that will naturally disappear in one to four weeks. The duration depends on the location of the body to which the stain is applied, the uptake of the stain, and the exposure of the epidermal area to which the stain is applied. For example, the epidermis is thicker on the sole of the foot than on the face, so a Mehndi design that is applied to the sole of the foot will last longer than one that is applied to the face. Further, the Mehndi designs will not last as long when the person having the design constantly washes their hands or is exposed to chemicals that remove or dry the epidermis increases sloughing of the skin and correspondingly decreases the duration of the decorative Mehndi stain.

Recently, tattoos have become increasingly popular in American culture. Some of the risks and generally undesirable characteristics associated with the application of or obtaining a tattoo are the permanence of the design, pain, cost, and the spread of HIV and hepatitis when the tattoo is applied in an unsterile fashion.

There are a number of undesirable features associated with the application of decorative Mehndi stains. First, having Mehndi past applied by a trained artist is quite costly. Second, the majority of the public does not have the artistic training needed to produce a design and have a satisfying result. Third, if the henna paste comes in contact with any exposed skin, then it will leave a stain, even if left on for a brief period of time. Fourth, if the henna past is not of the correct consistency, it will bleed beyond the line drawn and causing widening or blurring of the line that was intended to be drawn by the person applying the stain.

SUMMARY OF THE INVENTION

It is desirable to provide a method and apparatus for allowing an inexperienced person to apply decorative stains to a predetermined area of the epidermis. For this purpose, an adhesive stencil which includes an adhesive layer and a generally non-absorbent layer is used which has a number of advantages. First, the decorative patterns can be applied quite inexpensively. Second, the materials needed to make the stencil and the staining agent such as, for example, henna based die can be easily made and/or purchased on the market. Third, the use of an adhesive stencil having a generally non-absorbent layer allows for human error in that the design will not bleed. Fourth, the stencil allows the stain to be applied to any area of the body.

DETAILED DESCRIPTION OF THE INVENTION

Figure 1:
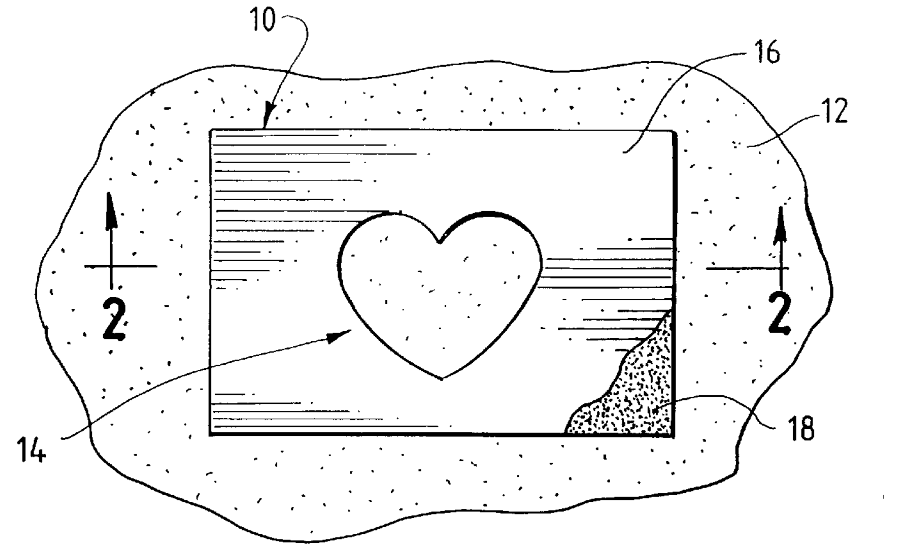
FIG. 1 is an elevational view of an embodiment of an adhesive stencil that is secured to the epidermal layer of the skin and allows a decorative stain to be applied to the area of the epidermis exposed through the stencil.
Figure 2:
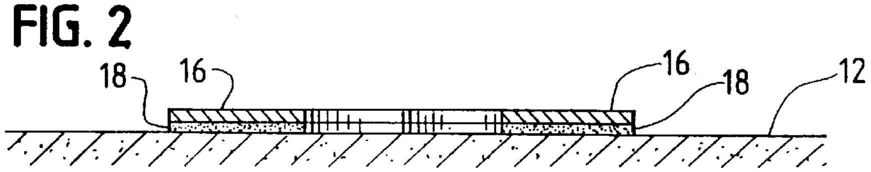
FIG. 2 is a sectional view taken along lines 2—2 of FIG. 1.

Referring to FIG. 1, an elevational view of a first embodiment of an adhesive stencil 10 is illustrated. Stencil 10 is secured to a predetermined area on the epidermis 12 of a person and includes a decorative pattern 14. Stencil 10 comprises a generally non-absorbent layer 16 that is secured to the epidermis 12 by means of a layer of adhesive 18 as shown in FIG. 2. In the embodiment shown in FIG. 1, the decorative pattern 16 comprises a one-piece cutout shaped as a heart.

Figure 4:
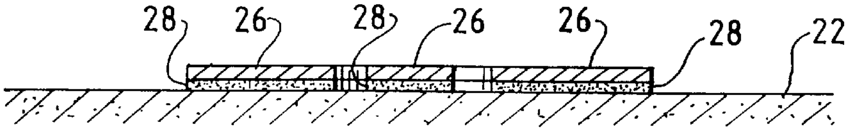
FIG. 4 is a sectional view taken along lines 4—4 of FIG. 3.

Referring to FIG. 2, a second embodiment of an adhesive stencil 20 is illustrated. Stencil 20 is secured to a predetermined area on the epidermis 22 of a person and includes a decorative pattern 24. Stencil 20 includes a generally non-absorbent layer 26 that is secured to the epidermis 22 of a person by means of a layer of adhesive 28 as shown in FIG. 4. In this embodiment, the decorative pattern comprises a two-piece cutout shaped as a cylinder.

It should be appreciated that the decorative patterns 14 and 24 shown in FIGS. 1 and 2 are merely illustrative and should not be interpreted to be limiting in any way. Particularly, the decorative patterns can be of any shape that is aesthetically pleasing for body art so long as the shape can be cut into an adhesive stencil by hand or by means of well know manufacturing techniques as readily apparent to one of ordinary skill in the relevant art. For example, a large number of the designs that currently are in use for tattooing purposes or other cope free designs can be utilized as a decorative pattern in an adhesive stencil according to this invention.

Stencils 10 and 20 may be manufactured from a number of suitable materials such as masking tape, adhering name badges, mailing stickers, surgical tape and the like by means of well know techniques readily apparent to one of ordinary skill in the relevant art. Multi-purpose labels that are readily commercially available from Avery® Dennison are preferred.

A henna-based die is suitable for use with an adhesive stencil to allow a decorative stain to be applied to the epidermis of a person. Preferably, a pre-made henna-based die is commercially available from Rani Kone™, a company in Pakistan. If desired, a quantity of henna-based die suitable for applying one decorative stain to the epidermis can be created by mixing two tablespoons of good quality henna power, two teaspoons of lemon juice and five to six teaspoons of black tea which contains one teaspoon of dissolved into a consistency similar to common household toothpaste. The citric acid in the lemon juice and the tea enhance the absorption of the henna powder into the epidermis. It should be appreciated that other types of epidermal stain materials suitable for use with the present invention include, for example, permanent markers, washable markers, and the like.

Figure 3:
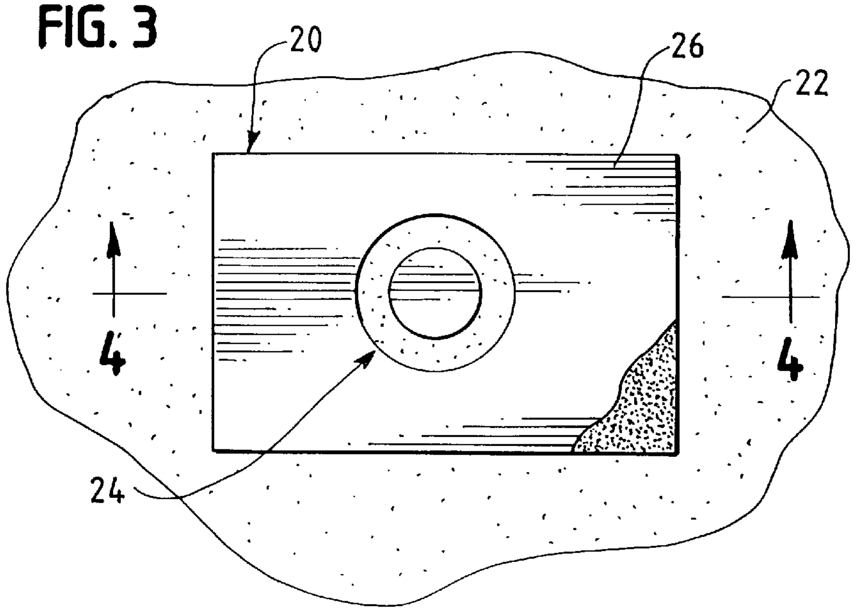
FIG. 3 is an elevational view of another embodiment of an adhesive stencil that is secured to the epidermal layer of the skin and allows a decorative stain to be applied to the area of the epidermis exposed through the stencil.

To apply a decorative stain to the epidermis, an adhesive stencil, such as those illustrated in FIGS. 1 and 2, is applied to a predetermined epidermal area on the skin. Next, a suitable quantity of an epidermal stain material such as, for example, a henna-based die is applied over the generally non-absorbent layer and decorative pattern in the adhesive stencil. The generally non-absorbent layer of the adhesive stencil prevents the epidermal stain material from seeping through the stencil and interfering with the clean application of a decorative epidermal stain. After the die is applied, the die is left on the adhesive stencil until it dries. Because the die is in a paste form, it adheres to the generally non-absorbent layer of the adhesive stencil. Typically, the drying period for the decorative patterns shown in FIGS. 1 and 3, each of which may be approximately one and one-half inches in length and width in use, is approximately three to four hours. After this time period, the adhesive stencil is removed which leaves a temporary tattoo in the shape of the decorative pattern as readily apparent to one of ordinary skill in the relevant art.

The temporary tattoo lasts anywhere from one to four weeks depending upon where the stain is applied. For example, a tattoo on the soles of the feet or the palms of the hands lasts much longer than one applied to the face because the epidermis is much thicker in the former epidermal areas than the latter.

While the invention has been illustrated and described in detail in the drawings and foregoing description, the same is considered as illustrative and not restrictive in character, it being understood that all changes and modification that come within the spirit of the invention are desired to be protected.

We claim:

1. A method for applying a decorative stain to the epidermis of a human, said method comprising the steps of:

applying a stencil having a decorative pattern formed therein to a predetermined area of said epidermis, said stencil comprising an adhesive layer for removably securing said stencil to said epidermis and an opaque non-absorbent layer coextensive with said adhesive layer;

covering said decorative pattern and a portion of the non-absorbant layer of said stencil with a predetermined amount of an epidermal stain material to cause said epidermal stain material to contact said epidermis only via the decorative pattern formed in said stencil;

drying said epidermal stain material, a portion of said epidermal stain material being absorbed into the portion of said epidermis that is coextensive with said decorative pattern to form a decorative stain in said epidermis in the form of said decorative pattern; and removing said stencil and the portion of said epidermal stain material that was not absorbed into said epidermis from said epidermis.

2. The method of claim 1 wherein said epidermal stain material comprises a henna-based die.

3. Apparatus for allowing a decorative stain to be applied to the epidermis of a human, comprising an adhesive stencil having a decorative pattern formed therein, said adhesive stencil including an adhesive layer for removably securing said stencil to said epidermis and an opaque non-absorbent layer coextensive with said adhesive layer, said stencil allowing a decorative stain to be applied to said epidermis by a method comprising the steps of:

covering said decorative pattern and a portion of the non-absorbant layer of said stencil with a predetermined amount of an epidermal stain material to cause said epidermal stain material to contact said epidermis only via the decorative pattern formed in said stencil, drying said epidermal stain material, a portion of said epidermal stain material being absorbed into the portion of said epidermis that is coextensive with said decorative pattern to form a decorative stain in said epidermis in the form of said decorative pattern, and removing said stencil and the portion of said epidermal stain material that was not absorbed into said epidermis from said epidermis.

4. The apparatus of claim 3 wherein said epidermal stain material comprises a henna-based die.

* * * * *